(12) United States Patent
Van Der Laan et al.

(10) Patent No.: US 8,773,657 B2
(45) Date of Patent: Jul. 8, 2014

(54) METHOD TO DETERMINE THE VALUE OF PROCESS PARAMETERS BASED ON SCATTEROMETRY DATA

(75) Inventors: Hans Van Der Laan, Veldhoven (NL); Rene Hubert Jacobus Carpaij, Vught (NL); Hugo Augustinus Joseph Cramer, Eindhoven (NL); Antoine Gaston Marie Kiers, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 1997 days.

(21) Appl. No.: 10/590,352

(22) PCT Filed: Feb. 22, 2005

(86) PCT No.: PCT/NL2005/000129
§ 371 (c)(1),
(2), (4) Date: May 21, 2007

(87) PCT Pub. No.: WO2005/081069
PCT Pub. Date: Sep. 1, 2005

(65) Prior Publication Data
US 2007/0222979 A1    Sep. 27, 2007

Related U.S. Application Data

(60) Provisional application No. 60/546,165, filed on Feb. 23, 2004.

(51) Int. Cl.
*G01J 1/10*    (2006.01)
(52) U.S. Cl.
USPC ..................... 356/243.1; 356/243.4
(58) Field of Classification Search
USPC .............. 356/601, 243.1–243.8; 700/121, 30, 700/108; 438/10, 17; 702/189, 155
See application file for complete search history.

(56) References Cited

U.S. PATENT DOCUMENTS

| | | |
|---|---|---|
| 6,622,059 B1 | 9/2003 | Toprac et al. |
| 6,917,901 B2 | 7/2005 | Bowley et al. |
| 2003/0048458 A1 | 3/2003 | Mieher et al. |

OTHER PUBLICATIONS

Allgair et al., "Spectroscopic CD Offers Higher Precision Metrology for sub-0.18 μm Linewidth Control", Yield Management—Yield Acceleration Strategies for the Semiconductor Industry, vol. 4, Issue 2, Summer 2002, pp. 8-13.
Wold et al., "Nonlinear PLS Modeling", Chemometrics and Intelligent Laboratory Systems, 7, pp. 53-65 (1989).
Valley et al., "Approaching New Metrics for Wafer Flatness: An Investigation of the Lithographic Consequences of Wafer Non-Flatness", Metrology, Inspection, and Process Control for Microlithography XVIII, Proceedings of SPIE, vol. 5375 (2004).

*Primary Examiner* — Tri T Ton
(74) *Attorney, Agent, or Firm* — Pillsbury Winthrop Shaw Pittman LLP

(57) ABSTRACT

A method according to an embodiment includes obtaining calibration measurement data, with an optical detection apparatus, from a plurality of marker structure sets provided on a calibration substrate. Each marker structure set includes at least one calibration marker structure created using different known values of the process parameter. The method includes obtaining measurement data, with the optical detection apparatus, from at least one marker structure provided on a substrate and exposed using an unknown value of the process parameter; and determining the unknown value of the process parameter from the obtained measurement data by employing regression coefficients in a model based on the known values of the process parameter and the calibration measurement data.

36 Claims, 9 Drawing Sheets

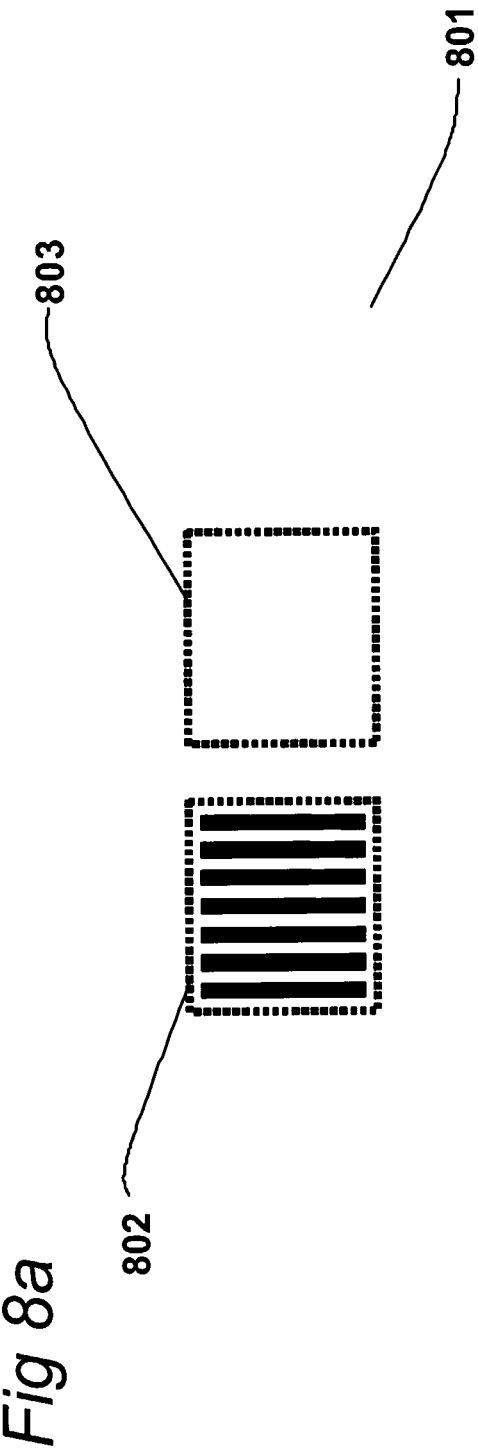
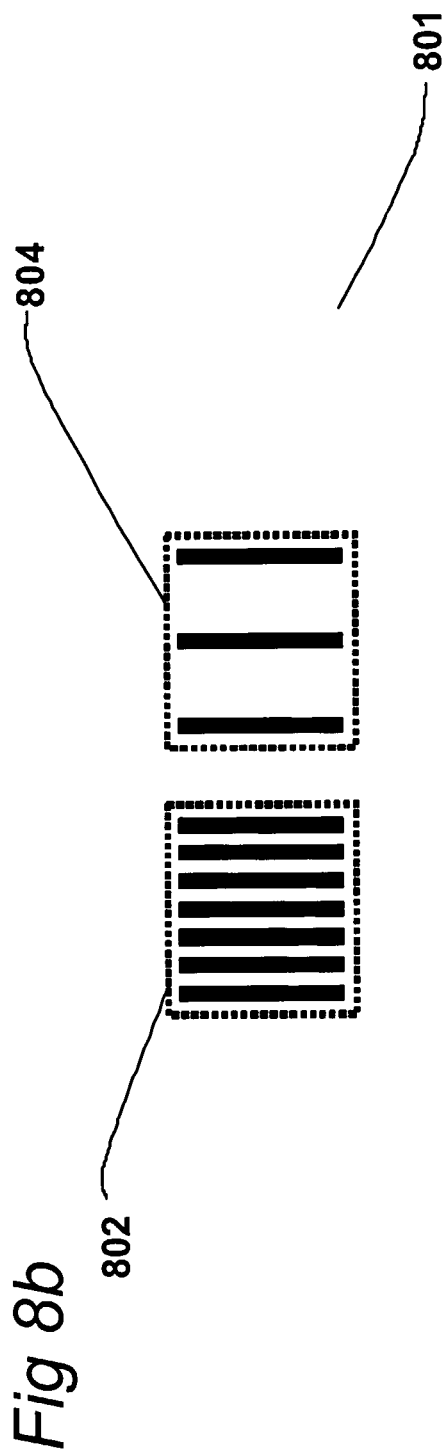
Fig 8a
Fig 8b

METHOD TO DETERMINE THE VALUE OF PROCESS PARAMETERS BASED ON SCATTEROMETRY DATA

This Application claims priority to U.S. Provisional Patent Application Ser. No. 60/546,165, filed Feb. 23, 2004, and to U.S. patent application Ser. No. 10/853,724, filed May 26, 2004, both documents being incorporated herein in its entirety by reference.

FIELD OF THE INVENTION

The present invention relates to a lithographic apparatus and methods.

BACKGROUND

A lithographic apparatus is a machine that applies a desired pattern onto a target portion of a substrate. Lithographic apparatus can be used, for example, in the manufacture of integrated circuits (ICs). In such a case, a patterning structure, such as a mask, may be used to generate a circuit pattern corresponding to an individual layer of the IC, and this pattern can be imaged onto a target portion (e.g. comprising part of, one or several dies) on a substrate (e.g. a silicon wafer) that has a layer of radiation-sensitive material (resist). In general, a single substrate will contain a network of adjacent target portions that are successively exposed. Known lithographic apparatus include so-called steppers, in which each target portion is irradiated by exposing an entire pattern onto the target portion at once, and so-called scanners, in which each target portion is irradiated by scanning the pattern through the projection beam in a given direction (the "scanning"-direction) while synchronously scanning the substrate parallel or anti-parallel to this direction.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist) or a metrology or inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

The terms "radiation" and "beam" used herein encompass all types of electromagnetic radiation, including ultraviolet (UV) radiation (e.g. having a wavelength of 365, 248, 193, 157 or 126 nm) and extreme ultra-violet (EUV) radiation (e.g. having a wavelength in the range of 5-20 nm), as well as particle beams, such as ion beams or electron beams.

The term "patterning structure" used herein should be broadly interpreted as referring to a structure that can be used to impart a beam of radiation (e.g. a projection beam) with a pattern in its cross-section such as to create a pattern in a target portion of the substrate. It should be noted that the pattern imparted to the beam may not exactly correspond to the desired pattern in the target portion of the substrate. Generally, the pattern imparted to the beam will correspond to a particular functional layer in a device being created in the target portion, such as an integrated circuit.

A patterning structure may be transmissive or reflective. Examples of patterning structures include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions; in this manner, the reflected beam is patterned.

The support structure supports, i.e. bares the weight of, the patterning structure. It holds the patterning structure in a way depending on the orientation of the patterning structure, the design of the lithographic apparatus, and other conditions, such as for example whether or not the patterning structure is held in a vacuum environment. The support can use mechanical clamping, vacuum, or other clamping techniques, for example electrostatic clamping under vacuum conditions. The support structure may be, for example, a frame or a table, which may be fixed or movable as required and which may ensure that the patterning structure is at a desired position, for example, with respect to the projection system. Any use of the terms "reticle" or "mask" herein may be considered synonymous with the more general term "patterning structure".

The term "projection system" used herein should be broadly interpreted as encompassing various types of projection system, including refractive optical systems, reflective optical systems, and catadioptric optical systems, as appropriate for example for the exposure radiation being used, or for other factors such as the use of an immersion fluid or the use of a vacuum. Any use of the term "lens" herein may be considered as synonymous with the more general term "projection system".

The illumination system may also encompass various types of optical components, including refractive, reflective, and catadioptric optical components configured to direct, shape, or control the projection beam of radiation, and such components may also be referred to below, collectively or singularly, as a "lens".

The lithographic apparatus may be of a type having two (dual stage) or more substrate tables (and/or two or more mask tables). In such "multiple stage" machines the additional tables may be used in parallel, or preparatory tasks may be carried out on one or more tables while one or more other tables are being used for exposure.

The lithographic apparatus may also be of a type wherein the substrate is immersed in a liquid having a relatively high refractive index, e.g. water, so as to fill a space between the final element of the projection system and the substrate. Immersion liquids may also be applied to other spaces in the lithographic apparatus, for example, between the mask and the first element of the projection system. Immersion techniques may be used to increase the numerical aperture of projection systems.

The continuous trend towards smaller design features and higher device densities requires high resolution lithography. In order to meet the requirements, it may be desirable to control the lithographic process in as many details as possible. Two of the most important process parameters that may need accurate monitoring and control are dose and focus. Generally the critical dimension (CD) variations are measured to monitor and control these parameters. However, it may be difficult to discriminate between dose and focus data when measuring CD-variations.

In general, special or multiple features are used in combination with special or time consuming metrology. The focus can for instance be determined by a phase shift focus monitor. The focus error results in an overlay error that can easily be detected with an overlay readout tool. In a second technique, the monitoring of the focus is achieved by using the concept of line-end shortening. However, with this technique the sign of defocus may be extremely difficult to determine. Additionally, most present-day techniques are only applicable on test structures.

The need to monitor the quality of the pattern that is exposed by a lithographic apparatus calls for a fast and reliable technique, which can be used at many locations, for example within a chip area or in a scribe line, on all kinds of substrates to be exposed, like test or product wafers. An optical metrology technique, called scatterometry, can meet these requirements to a certain extent. The terms "optical" and "light" used herein encompass all types of electromagnetic radiation, including light with a wavelength of 400-1500 nm, ultraviolet (UV) radiation (e.g. having a wavelength of 365, 248, 193, 157 or 126 nm) and extreme ultraviolet (EUV) radiation (e.g. having a wavelength in the range of 5-20 nm), as well as particle beams, such as ion beams or electron beams.

In scatterometry, a light beam is directed towards a target, generally a specially designed structure like a diffraction grating. Then, the target reflects, refracts and/or diffracts the light. Finally the light from the target can be detected by a detector including a suitable sensor. The detection by the detector can be in reflection or in transmission, measuring the diffracted and/or non-diffracted light. For the incoming light, i.e. the light directed at the target, one or more sets of properties can be varied simultaneously. The terms "scatterometry" and "scatterometer" used herein encompass all types of measurement techniques and tools in which light is generated and analyzed after interaction with a target. The term "scatterometer" thus includes, for example, an ellipsometer and a scanning electron microscope (SEM). The term "spectrum" used herein encompasses all types of formats in which the light after interaction with the target can be detected. It thus includes images created by scattered electrons in a SEM.

Scatterometry is conventionally used to determine the values of process parameters, like focus and dose. Generally, however, several assumptions are made regarding the relationship between process parameters and scatterometry measurement parameters. Examples of such assumed relationships are a linear relationship between focus and side wall angle (the slope at the side of a line-shaped structure) and a linear relationship between dose and mid-CD (the width of a line-shaped structure at half its height). In reality, there may be no unique relationship between one single scatterometry measurement parameter and a process parameter like focus or dose. There may be, for example, additional effects, besides focus, that contribute to the characteristics of a side wall angle. By the aforementioned assumption, these effects would then be abusively interpreted as focus.

The detected spectrum (or, in the case where particle beams are used, the detected signal may be an image rather than a spectrum) is analyzed by comparing it with data, stored in a library. A so-called "best match" between the detected spectra and the spectra in the library determines the parameter values that best describe the target structure. For lithographic purposes, the identified parameter values, i.e. focus and dose, can be applied to increase the performance of a lithographic apparatus. The quality of lithographic process parameter control and monitoring may strongly depend on the quality of the library. A library is generally filled with theoretical spectra constructed by calculating values for different scatterometry measurement parameters such as grating parameters like grating height, line width and side wall angle, and different substrate parameters, such as material properties and properties related to layers in the substrate processed earlier. It can easily be understood that the creation of an extremely reliable library can be time-consuming and highly complex, especially when the properties of the substrates to be exposed change regularly.

Furthermore, scatterometry measurement parameters, like the thickness of the underlying layers and the optical constants of the used materials, may be extremely difficult to determine in a production situation. The use of empirical data, i.e. experimentally obtained data, has been suggested. (See for instance Allgair et al., Yield Management Solutions, Summer 2002, pp 8-13). In such a case, the empirical library is then generated from a substrate with a number of structures processed by a varying set of process parameters covering the process space to be controlled. However, as mentioned in this reference, the characterization of these structures is nontrivial, due to the required level of control over the process parameters and an important influence of noise introduced by 'natural variation', i.e. not deliberately induced variations.

SUMMARY

Embodiments of the invention include methods for determining at least one process parameter related to a lithographic method, which employs empirical data. One embodiment provides a method for determining at least one process parameter, the method comprising:

obtaining calibration measurement data from a plurality of calibration marker structure sets provided on a calibration object, each of said plurality of calibration marker structure sets comprising at least one calibration marker structure, calibration marker structures of different calibration marker structure sets being created using different known values of said at least one process parameter;

determining a mathematical model by using said known values of said at least one process parameter and by employing a regression technique on said calibration measurement data, said mathematical model comprising a number of regression coefficients;

obtaining measurement data from at least one marker structure provided on an object, said at least one marker structure being made using an unknown value of said at least one process parameter; and determining the unknown value of said at least one process parameter for said object from said obtained measurement data by employing said regression coefficients of said mathematical model.

In another embodiment of the invention, there is provided a system for determining at least one process parameter, the system comprising:

a detector arranged to obtain calibration measurement data from a plurality of calibration marker structure sets provided on a calibration object, each of said plurality of calibration marker structure sets comprising at least one calibration marker structure, calibration marker structures of different calibration marker structure sets being created using different known values of said at least one process parameter;

a processor unit storing a mathematical model determined by using said known values of said at least one process parameter and by employing a regression technique on said calibration measurement data, said mathematical model comprising a number of regression coefficients;

said processor unit being arranged to obtain measurement data from at least one marker structure provided on an object, said at least one marker structure being made using an unknown value of said at least one process parameter; and to determine the unknown value of said at least one process parameter for said object from said obtained measurement data by employing said regression coefficients of said mathematical model.

In an embodiment of the present invention the system comprises a lithographic apparatus comprising an illumination system configured to provide a projection beam of radiation; a support structure configured to support a patterning structure, the patterning structure serving to impart the beam of radiation with a pattern in its cross-section; a substrate table configured to hold the substrate; and a projection system configured to project the patterned beam onto a target portion of the substrate.

In an embodiment of the invention, there is provided a semiconductor device produced with the method of the present invention according to any of the embodiments disclosed herein.

In an embodiment the system includes a lithographic apparatus including an illumination system configured to provide a beam of radiation; a support structure configured to support a patterning structure, the patterning structure serving to impart the beam of radiation with a pattern in its cross-section; a substrate table configured to hold a substrate with at least one marker structure; and a projection system configured to project the patterned beam onto a target portion of the substrate.

The invention further relates to a semiconductor device manufactured with the system according to any of the aforementioned embodiments.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIGS. 8a, 8b depict a top view of different combinations of marker structures according to an embodiment of the invention.

DETAILED DESCRIPTION

Figure 1:
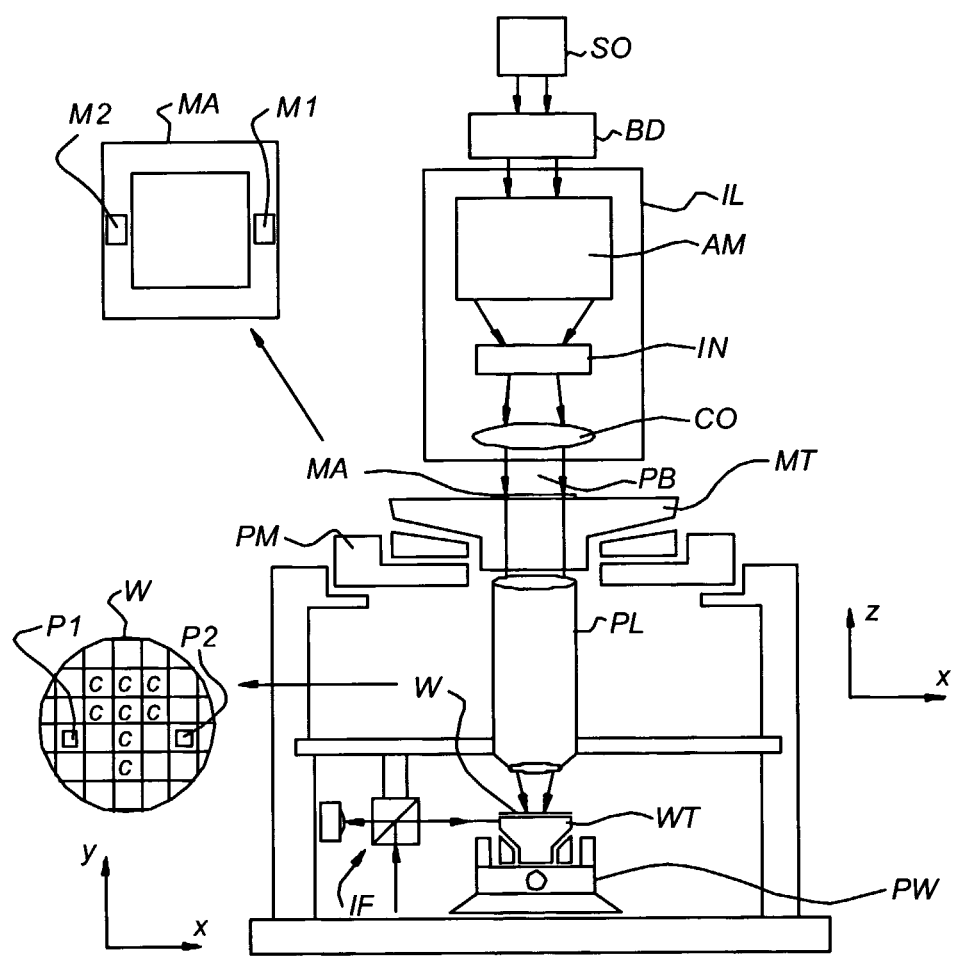
FIG. 1 depicts a lithographic apparatus according to an embodiment of the invention.

FIG. 1 schematically depicts a lithographic apparatus according to an embodiment of the invention. The apparatus includes an illumination system (illuminator) IL configured to provide a projection beam PB of radiation (e.g. UV radiation or radiation with other wavelengths), and a first support structure (e.g. a mask table) MT configured to support a patterning structure (e.g. a mask) MA and connected to a first positioning device PM configured to accurately position the patterning structure with respect to the projection system, item PL. The apparatus further includes a substrate table (e.g. a wafer table) WT configured to hold a substrate (e.g. a resist-coated wafer) W and connected to second positioning device PW configured to accurately position the substrate with respect to the projection system ("lens"), PL, the projection system (e.g. a refractive projection lens) PL ("lens") being configured to image a pattern imparted to the projection beam PB by a patterning structure MA onto a target portion C (e.g. comprising one or more dies) of the substrate W.

As here depicted, the apparatus is of a transmissive type (e.g. employing a transmissive mask). Alternatively, the apparatus may be of a reflective type (e.g. employing a programmable mirror array of a type as referred to above).

The illuminator IL receives a beam of radiation from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising for example suitable directing mirrors and/or a beam expander. In other cases the source may be integral part of the apparatus, for example when the source is a mercury lamp. The source SO and the illuminator IL, together with the beam delivery system BD if required, may be referred to as a radiation system.

The illuminator IL may include an adjusting device AM configured to adjust the angular intensity distribution of the beam. Generally, at least the outer and/or inner radial extent (commonly referred to as σ-outer and σ-inner, respectively) of the intensity distribution in a pupil plane of the illuminator can be adjusted. In addition, the illuminator IL generally includes various other components, such as an integrator IN and a condenser CO. The illuminator provides a conditioned beam of radiation, referred to as the projection beam PB, having a desired uniformity and intensity distribution in its cross-section.

The projection beam PB is incident on the mask MA, which is held on the mask table MT. Having traversed the mask MA, the projection beam PB passes through the lens PL, which focuses the beam onto a target portion C of the substrate W. With the aid of the second positioning device PW and position sensor IF (e.g. an interferometric device), the substrate table WT can be moved accurately, e.g. so as to position different target portions C in the path of the beam PB. Similarly, the first positioning device PM and another position sensor (which is not explicitly depicted in FIG. 1) can be used to accurately position the mask MA with respect to the path of the beam PB, e.g. after mechanical retrieval from a mask library, or during a scan. In general, movement of the object tables MT and WT will be realized with the aid of a long-stroke module (coarse positioning) and a short-stroke module (fine positioning), which may form part of the positioning devices PM and PW. However, in the case of a stepper (as opposed to a scanner) the mask table MT may be connected to a short stroke actuator only, or may be fixed. Mask MA and substrate W may be aligned using mask alignment marks M1, M2 and substrate alignment marks P1, P2.

The depicted apparatus can be used in the following preferred modes:

1. In step mode, the mask table MT and the substrate table WT are kept essentially stationary, while an entire pattern imparted to the projection beam is projected onto a target portion C in one go (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the projection beam is projected onto a target portion C (i.e. a single dynamic exposure). The velocity and direction of the substrate table WT relative to the mask table MT is determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning structure, and the substrate table WT is moved or scanned while a pattern imparted to the projection beam is projected onto a target portion C. In this mode, generally a pulsed radiation source is employed and the programmable patterning structure is updated as required after each movement of the substrate table WT or in between successive radiation pulses during a scan. This mode of operation can be readily applied to maskless lithography that utilizes programmable patterning means, such as a programmable mirror array of a type as referred to above.

Combinations and/or variations on the above described modes of use or entirely different modes of use may also be employed.

Figure 2:
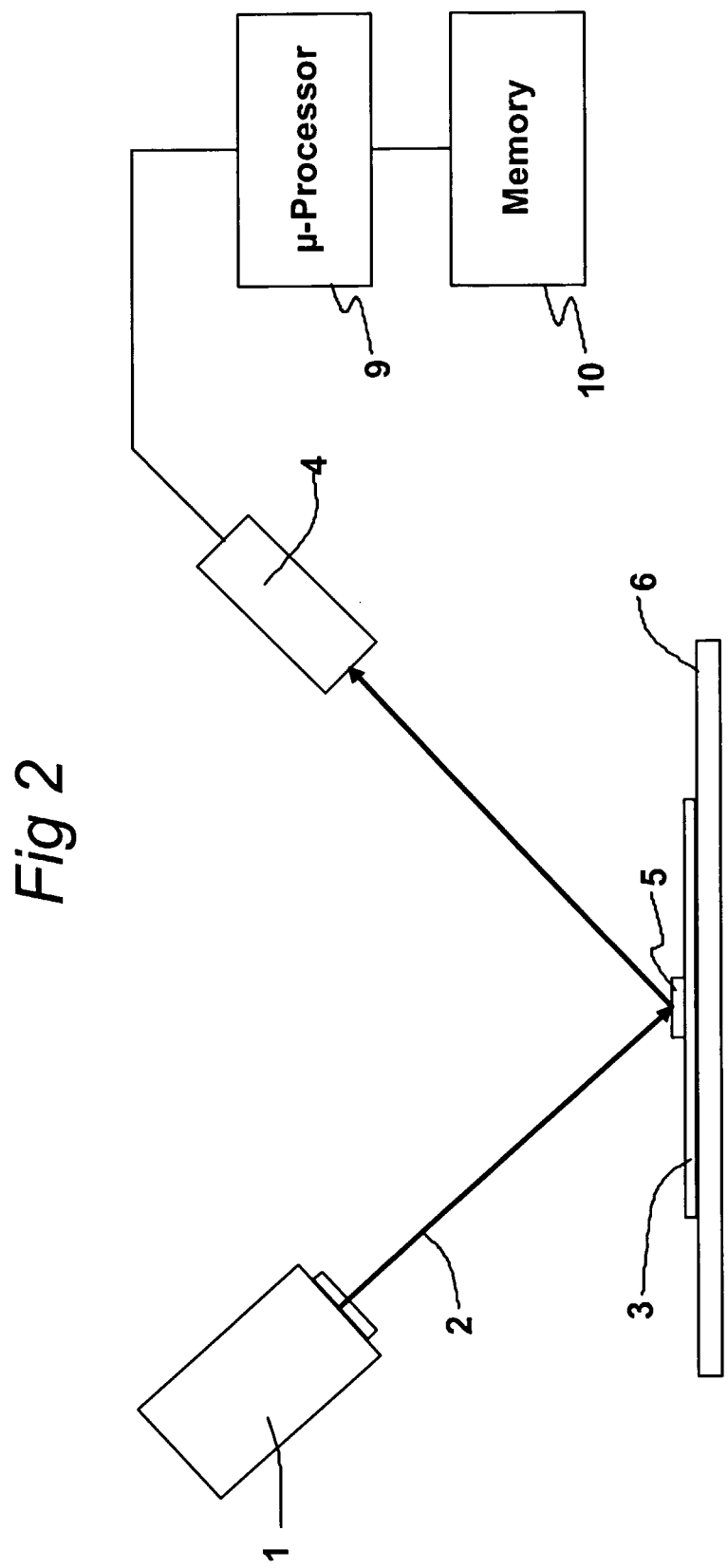
FIG. 2 depicts a state-of-the-art scatterometer.

FIG. 2 depicts a state-of-the-art scatterometer. The scatterometer includes a light source 1, which directs a light beam 2 towards a structure 5, generally some type of grating, on a substrate 3 to be exposed, lying on a substrate table 6, and a detector 4. The detector 4 is connected to a (micro)processor 9, which is connected to a memory 10. The light beam 2 reflects and/or diffracts at the suitable structure 5 positioned on the surface of the substrate 3. The spectrum of the reflected light beam is detected by the detector 4. The light beam 2 may be directed towards the substrate 3 at an angle, as shown in FIG. 2, but may also be directed perpendicular to the substrate 3. There are several scatterometry concepts, in which one or more sets of properties of the light, which is directed to the suitable structure, can be varied simultaneously. Examples of a set of properties are a set of wavelengths, a set of angles of incidence, a set of polarization states or a set of phases and/or phase differences. The detector can be arranged to detect one or a combination of the aforementioned sets, and may include one or more sensors to record different parts of the reflected and/or diffracted light.

Figure 3:
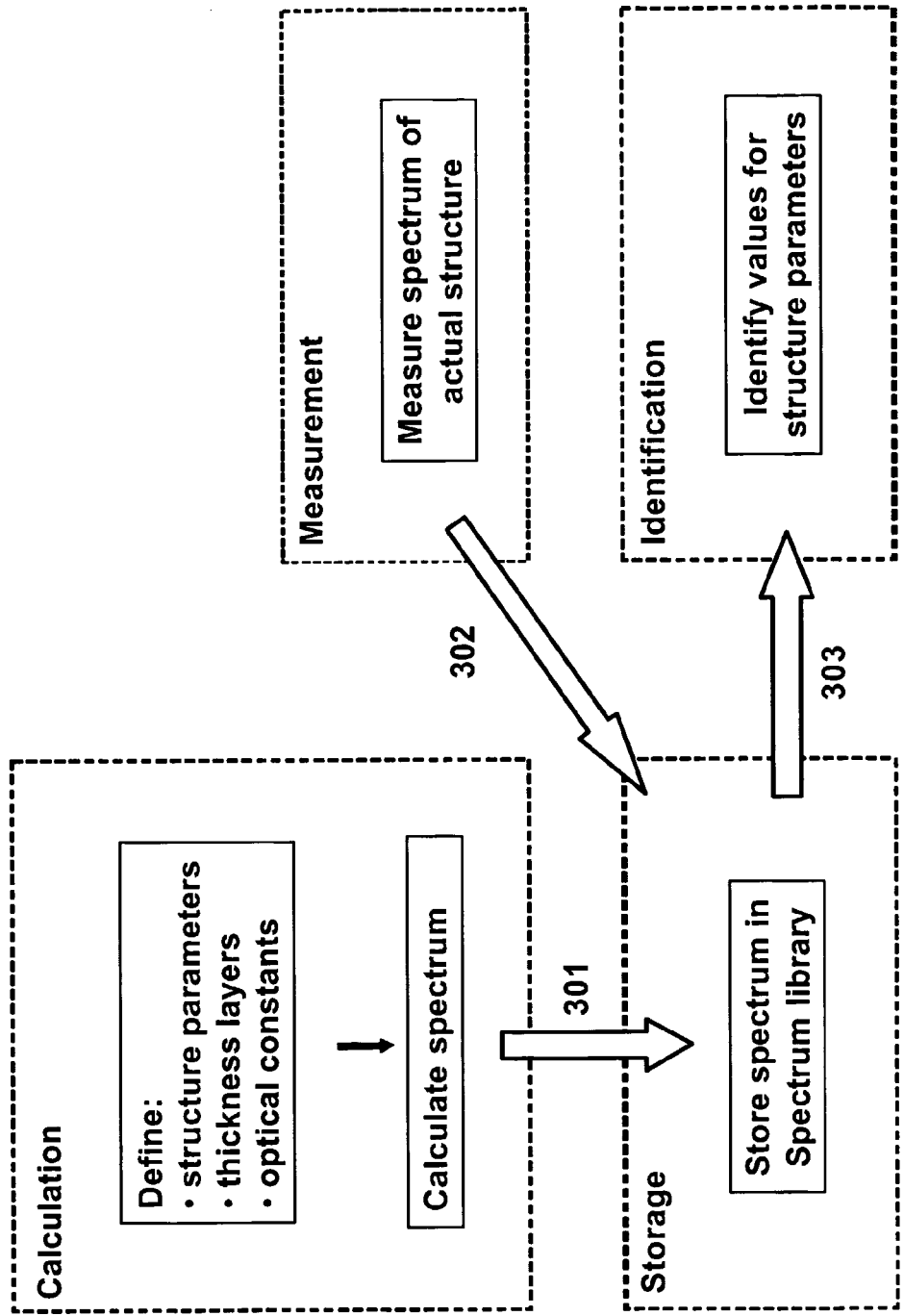
FIG. 3 depicts a functional flow of a library-based method.

FIG. 3 depicts a functional overview of a use of a library-based method in scatterometry. The library may be generally constructed by calculating the spectrum for different scatterometry measurement parameters, e.g. structure parameters like line width, line height, side wall angle etc. of the lines of structure 5, thickness of the underlying (non-patterned) layers below such lines and the optical constants of all the materials that interact with the light beam 2. Before a measurement on a real physical structure 5, the aforementioned parameters related to this specific kind of structure 5 may need to be defined. For a predetermined range of each of these defined parameters, a spectrum of the light modulated by the structure 5 is calculated and stored, in task 301, by processor 9 in a spectrum library of memory 10.

Theoretical calculations can then be performed on known structures, as will be appreciated by one skilled in the art. For example, when the library is filled by processor 9 with enough spectra to cover the expected area of performance of the spectrum of an actual structure 5 to be measured, a measurement on the actual structure 5 is performed. The method then proceeds to task 302, where the measured spectrum of the actual structure 5 is then compared by processor 9 with the plurality of stored spectra in the spectrum library of memory 10. Alternatively, real time fitting can also be applied.

Next, by using an interpolation algorithm, a 'best match' is extracted in task 303 from memory 10, and the values of the parameters, which correspond to the parameters that were used to generate the extracted spectrum, are identified. For example, when the measured spectrum has a best resemblance to a spectrum that is constructed by using a value A1 for a parameter A and a value B3 for a parameter B, processor 9 eventually gives the output {A1, B3}.

A rigorous diffraction modeling algorithm, like Rigorous Coupled Wave Analysis (RCWA), may be used to compute the spectra of the spectrum library. This complex algorithm, which is used to calculate the spectra that are stored in the spectrum library of memory 10, may require, among other aspects, a forehand knowledge of the optical properties of the materials that are used. In practice, especially for product wafers, only the values of some of these properties are known, and therefore approximations are generally used. Moreover, in a production situation, the properties of different structures in underlying layers are insufficiently known. As a result, conventional library-based methods may be complex, which may limit routine use in production situations.

In the following description, reference will be made to dose and focus as exemplary process parameters. However, it should be understood that embodiments of the invention may be applied in a similar fashion when other lithographic process parameters are used. Other examples of process parameters that can be used include, for example, track parameters related to dose, variation of line width over a reticle, variations from reticle-to-reticle, projection lens aberrations, projection lens flare, and angular distribution of light illuminating the reticle.

Figure 4:
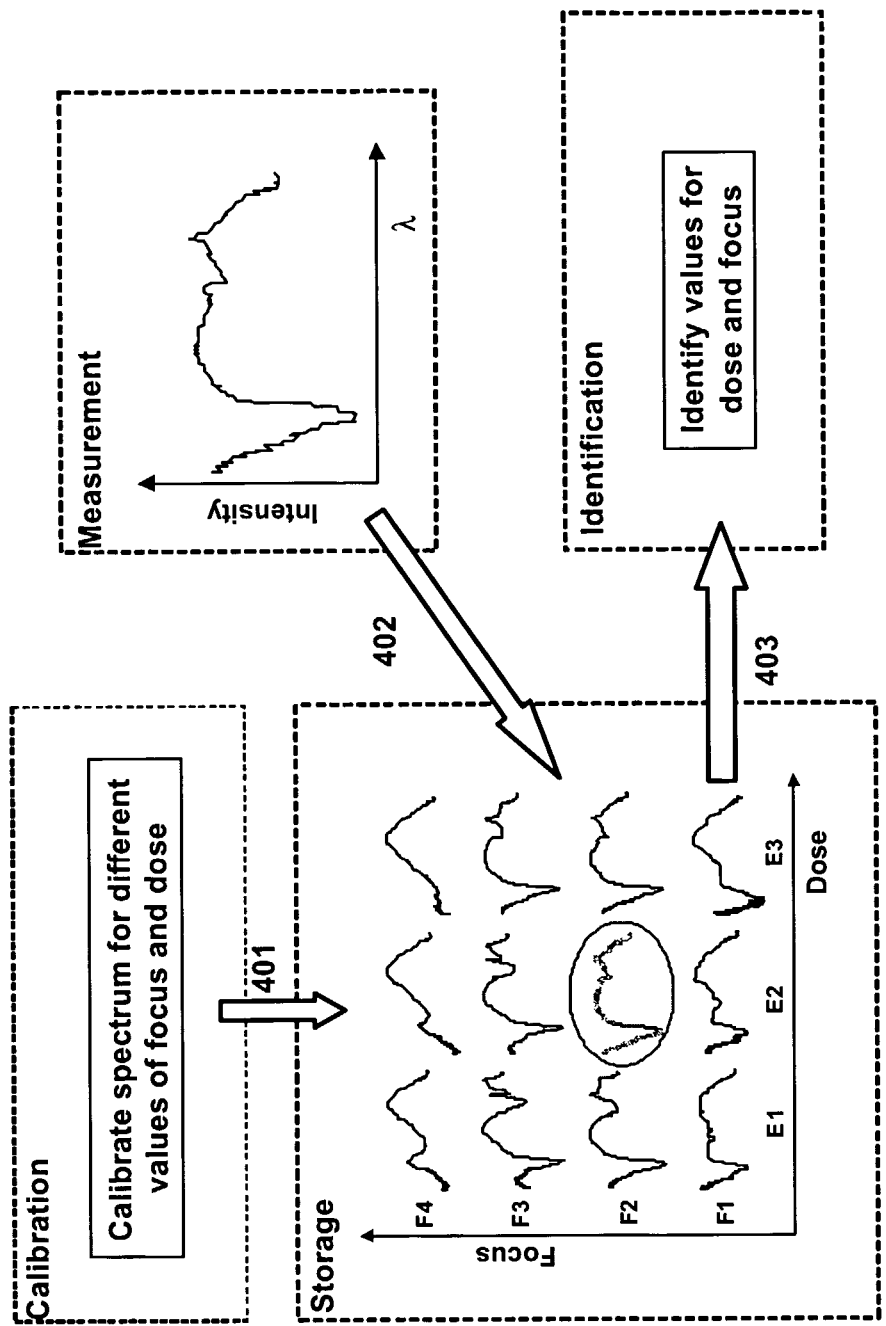
FIG. 4 depicts a functional flow of a library-based method using measured calibration spectra.

FIG. 4 depicts a functional representation of a library-based method of scatterometry, according to an embodiment of the invention. In this method, measured calibration spectra, instead of theoretical spectral data, are directly used and compared with a measured spectrum on an actual physical structure, which can be, for example, a diffractive structure like a grating. Before performing a measurement of the actual, physical structure, a calibration is performed on a calibration substrate.

In an embodiment of the invention, the calibration substrate is provided with a plurality of calibration structures, each of the calibration structures having a substantially comparable shape as the physical structure to be measured. Each of the calibration structures may have a unique position on the calibration substrate, and is built with a combination of unique values of process parameters, like focus and exposure (dose). In an embodiment of the invention, the value of a first process parameter is varied in a first direction across the substrate, while in a second direction, which is substantially perpendicular to the first direction, a second process parameter may be varied. In an embodiment of the invention, the first and second process parameters are focus and dose. In such a case, the calibration substrate is called a Focus-Exposure Matrix (FEM). In the following description, reference will be made to the FEM to explain a concept of embodiments of the present invention. However, it will be appreciated that alternative matrices may be used in other embodiments of the invention.

In an embodiment of the invention, the method begins in task 401, where calibration spectra are measured with the FEM, are then stored in memory 10, together with information regarding the values of focus and dose, which were used to manufacture them. Next, the spectrum of light impinging on the actual, physical structure is measured. This measured spectrum is then compared in task 402 with the spectra stored in memory 10. The method then proceeds to task 403, where a 'best match' is extracted from memory 10. At this stage, the values of dose and focus are derived from the extracted spectrum. For example, in FIG. 4 the 'best match' between the measured spectrum and the spectra measured on the structures provided by the FEM is determined to be the spectrum that corresponds with the value F2 for focus and the value E2 for exposure (dose).

It will be appreciated that a potential advantage of at least some embodiments as illustrated in FIG. 4 is that no forehand knowledge of optical properties of materials is required to determine the parameters. However, as in any library-based methods as described above, the determined values of selected process parameters are discretised. Furthermore, noise introduced in the calibration task by 'natural variation', i.e. not deliberately induced variations, may have a significant influence on the identification of the values of the selected process parameters. It may be desirable to minimize the disturbance of the identification caused by this natural variation.

Sources of natural variation may include the following. In a scanner, natural variation may relate to random focus and exposure dose errors which will be different for each individual exposure with its unique focus & dose setting. In a track, natural variation may relate to non-uniform processing across the wafer (these are partly dose related). In a wafer, natural variation may relate to non-uniform underlying layers across the wafer. In a scatterometer, natural variation may relate to thermal, mechanical and electrical noise.

Figure 5A:
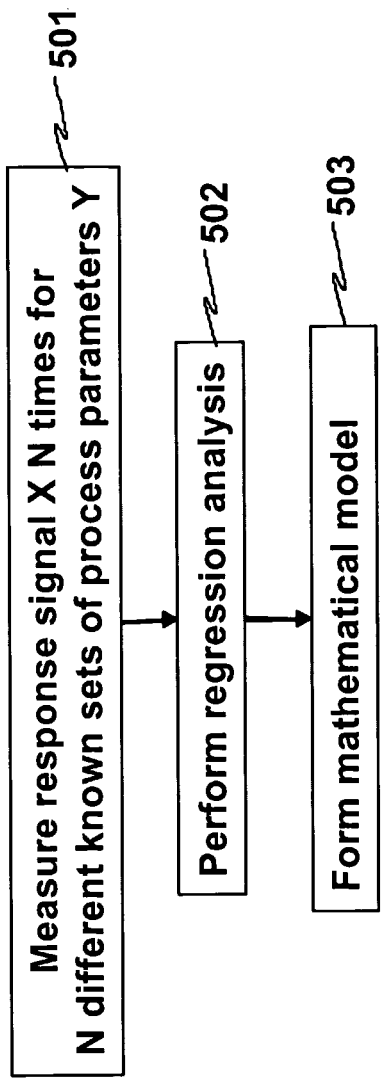
FIGS. 5a, 5b depict a functional block diagram representing two phases according to an embodiment of the present invention.
Figure 5B:
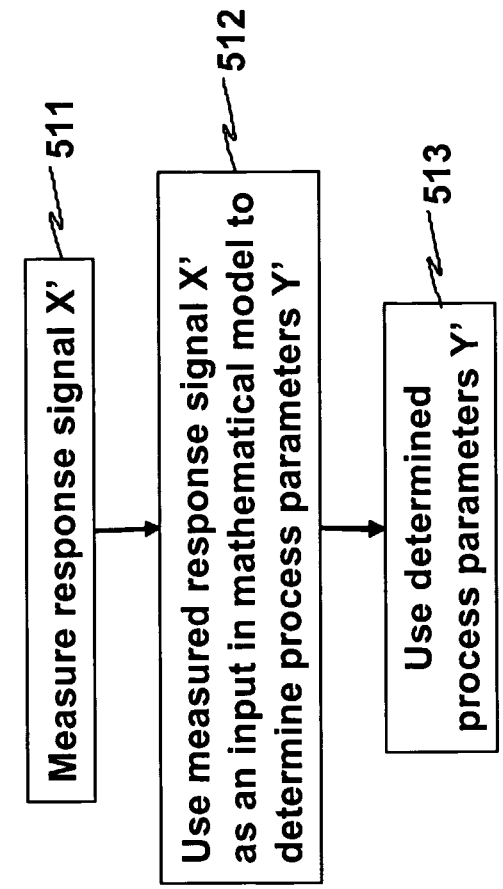

FIGS. 5*a*, 5*b* show functional block diagrams of an embodiment of the present invention. In this embodiment, calibration spectra are used to form a mathematical model by employing a regression technique in a calibration phase. Then, the process parameters that were used to manufacture a real structure to be measured upon, can be derived by employing the obtained mathematical model in an operational phase. FIG. 5*a* depicts the method used in the calibration phase, in one such embodiment of the invention. The method starts at task 501, where calibration spectra are measured with a number of calibration structures and stored in a memory 10. These calibration structures are constructed with a known set of process parameters, which are different for each calibration structure. For example, when the process parameters are focus and dose, the method first measures the calibration structures with a FEM and stores the measured spectra in a memory 10.

The method then proceeds to task 502, where a regression analysis is performed on the stored calibration spectra with a processor connected to the memory 10. This processor can be processor 9 in an embodiment of the invention or may be a different processor in other embodiments of the invention. Next the method proceeds to task 503, where a mathematical model, which is stored in a memory, is determined. The mathematical model defines a relationship between the calibration spectra and the process parameters used to manufacture the calibration structure upon which the calibration spectra are measured. The memory can be memory 10, in an embodiment of the invention, but may also be a different memory, connected to the processor, in other embodiments of the invention.

FIG. 5*b* shows a method according to an embodiment of the invention, which may be performed by processor 9, to use the obtained model to derive the values of selected process parameters from measurements performed on a "real" structure on a substrate. The method starts in task 511, where a response signal is measured on the "real" structure on a substrate. The measured signal, which can be a spectrum, serves as an input for the model. The method then proceeds to task 512, where the desired values of the selected process parameters are determined. Next, the method proceeds to task 513, where the determined process parameters are used in the lithographic process, either manually or automatically, to correct, for example, external settings of the lithographic apparatus, like dose settings, focus settings, positioning settings (e.g. movement of substrate table WT) etc.

It will be appreciated that the effects of natural variation may be minimized in embodiments of the present invention. Because the natural variation of a selected process parameter is included in the calibration, the created model may be independent of the natural variation of this process parameter. In order to better minimize the effects of natural variation, it may be desirable to use a random variation (e.g. the calibration wafer may be made such that this is the case). Moreover, if the natural variation of a process parameter is known, it can be used as a separate input in the formation of the model in the calibration phase. Here, "separate" means either additional input or that it can replace the deliberately induced process offsets.

The regression technique, used in the regression method, can be either linear or non-linear, in an embodiment of the invention. A neural network can also be used, in an embodiment of the invention. Such techniques may be applied to provide interpolation, i.e. between the calibration points of the model, and/or noise reduction.

Figure 6:
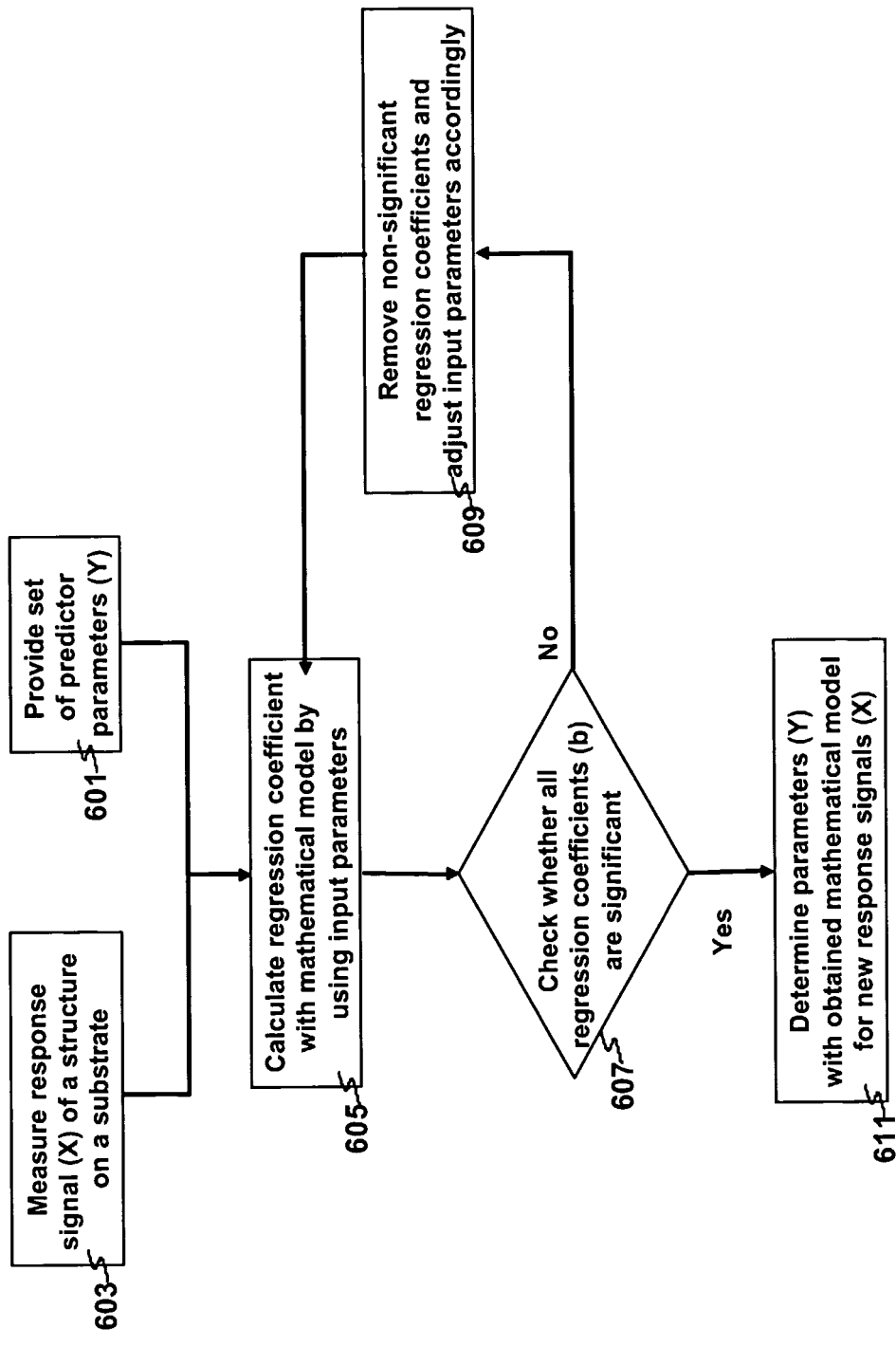
FIG. 6 depicts a functional block diagram of the concept of regression, according to an embodiment of the invention.

A functional block diagram of a regression technique according to another embodiment of the present invention, is depicted in FIG. 6. The concept is based on an iteration process, wherein a measured response signal X and a set of predictor parameters Y are used to calculate regression coefficients b, which combine X and Y, thus forming a mathematical model. Predictor parameters Y are parameters related to the process parameters under examination. The method starts in task 601, where a set of predictor parameters Y is provided and then proceeds to task 603, where a response signal X of a structure on a substrate is measured. Both the predictor parameters Y and measured response signal X serve as an input for the mathematical model, which calculates in task 605, the modeled regression coefficients b. Then, in task 607, the significance of all of the regression coefficients b is checked. This control task determines whether the mathematical model is robust or not. Regression coefficients, which are not significant, are removed from the mathematical model in task 609 and the regression is repeated with the reduced number of regression coefficient. Tasks 605 and 607 are repeated until all of the regression coefficients in the mathematical model are significant. Then, the method proceeds to task 611, where regression results are used to determine predictor parameters Y for the new response signals X.

In an embodiment of the invention, a linear regression (MLR) can be used to turn data into information. Suitable situations develop when there are few response signals, sometimes also referred to as factors. In cases where the factors are not significantly redundant, i.e. they are collinear, or when they have a well-understood relationship with predictor parameters Y, MLR can be very useful. However, if any of these three conditions is not fulfilled, MLR can be inefficient or inappropriate. Embodiments of the invention include methods in which MLR is applied based on the presence of one or more such conditions.

In an embodiment of the present invention, spectra, measured by scatterometry, are used to estimate values of lithographic process parameters, like dose and focus. Generally, the factors that include a spectrum, number in the hundreds and are highly collinear. The predictor parameters Y are in this case the values of the lithographic process parameters.

Figure 7A:
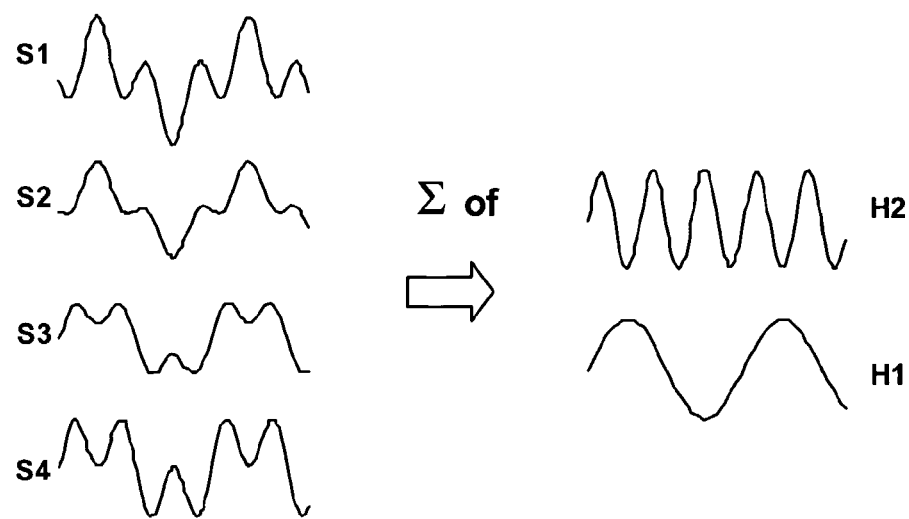
FIGS. 7a, 7b show the concept of partitioning in harmonics and the concept of partitioning in principal components, according to an embodiment of the present invention.
Figure 7B:
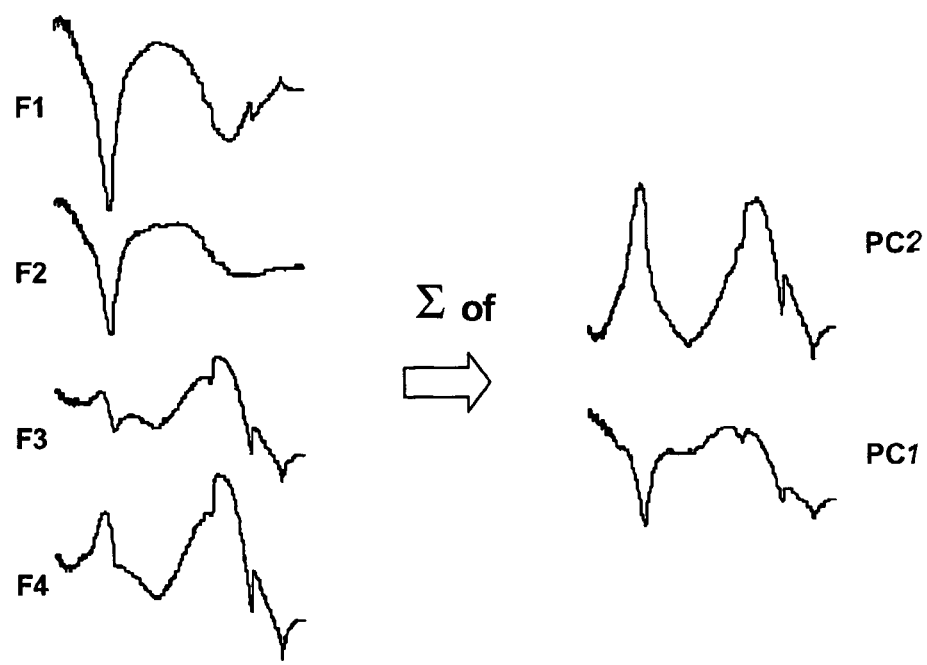

FIGS. 7a, 7b show examples of decomposition techniques that may be used in embodiments of the invention. The first technique, depicted in FIG. 7a, uses a Fourier analysis, which is based on the principle that a signal can be described by a sum of basic harmonic functions, wherein each function contributes with a certain weight factor. For example signals S1, S2, S3 and S4 in FIG. 7a can be described as a sum of H1 and H2 with weight factors [1,−1], [1,−½], [1,+½] and [1,1] respectively.

The second technique is a similar technique based on the principle that a signal can be described as a sum of a number of principal components, each of the principal components contributing with a certain weight factor. The number of principal components may vary considerably. FIG. 7b shows four exemplary scatterometry spectra (F1, F2, F3 and F4) that can be described by combining principal components PC1 and PC2 with weight factors [1,−1], [1,−½], [1,+½] and [1,1] respectively. Decomposition techniques, like those mentioned above but not limited to these examples, may be employed in an embodiment of the present invention for the regression analysis. For example, in the case of the principal component regression (PCR), the principal components extracted from the measured response signal X may serve as an input for the mathematical model instead of the X-factors as depicted in FIG. 6.

Besides the two depicted decomposition techniques, other techniques of decomposition may also be employed in embodiments of the present invention. Examples of these techniques include decomposition techniques that are based on the concept of partial least squares (PLS) modeling and non-linear PLS modeling, as described, for example, in Wold et al. Chemometrics and Intelligent Laboratory Systems, 7 (1989) 53-65.

Before the spectral data is fed to the model, some kind of pre-processing may be applied, in an embodiment of the invention. Pre-processing can enhance the results of the model. Examples of pre-processing operations that may be applicable to the present invention are subtraction of the mean, division by standard deviation and weighting or selection of scatterometric variables like angle, wavelength and polarization state. As a result, data at certain wavelengths can be removed before the data is fed to the model.

In embodiments of the present invention, more than one type of marker structure can also be used in both the calibration and measurement process. Thus, the invention is applicable to multiple calibration structure sets where each set comprises one or more (different) calibration structures. Thus, each set may comprise one or more calibration structures, in which it is possible that the number of calibration structures per calibration structure set varies. Furthermore, the calibration structures within and/or between calibration structure sets may be different. It may be desirable that, within each set, the different types of marker structures be positioned in close proximity to each other on the calibration substrate. It may also be desirable that the calibration measurement and sample measurement be substantially identical in at least some respects (e.g. same pre-processing, same marker or combination of marker, and/or same wafer type). The obtained spectra on these markers can be appended to each other, before they are used by the mathematical model. However, it may also be possible to combine those spectra, in an embodiment of the invention, by some kind of mathematical operation, resulting in one combined "spectrum" that is used by the model.

FIGS. 8a, 8b show a top view of a calibration substrate 801 that is provided with a combination of marker structures, which can be employed in an embodiment of the present invention. In FIG. 8a, a first marker structure 802 includes a pattern that is formed on top of a number of non-patterned layers. A second marker structure 803 does not include the pattern and is only formed by the non-patterned layers. In FIG. 8a, only one set with first and second marker structures 802, 803 is shown. However, in order to perform the calibration method of the present invention, several such sets are produced on the same calibration substrate 801 using different process parameters for the different sets. In a scatterometry measurement, the second marker structure 803 only reflects the variations within the non-patterned layer, while the pattern of the first marker structure 802 adds its contribution to these non-patterned layer contributions. The scatterometry measurement results, obtained on the second marker structure 803, can now be used to reduce the non-patterned layer contribution in the scatterometry measurement result obtained on the first marker structure 802. Examples of operations that may perform this reduction include subtracting the spectrum of the second marker structure 803 from the spectrum of the first marker structure 802, and fitting the spectrum of the second marker structure 803 to the spectrum of the first marker structure 802, then using the residual as an input for the mathematical model.

In FIG. 8b, a different combination of a set of two marker structures on substrate 801, according to an embodiment of the invention, is depicted. Although FIG. 8b shows one set, in order to perform the method of the invention a plurality of such sets will be produced on the substrate while using different process parameters for different sets. The first marker structure 802 includes e.g. the same pattern as the first marker structure 802 in FIG. 8a. However, contrary to the second marker structure 803 of FIG. 8a, the second marker structure 804, which is shown in FIG. 8b, is patterned. In this embodiment of the invention, both marker structures 802, 804, are patterned, but the patterns of each marker structure are different. Because the marker structures will have a different sensitivity for the lithographic process parameters, a better separation of the process parameters may be possible. It will be appreciated that other combinations of patterned marker structures can be employed in other embodiments of the present invention. In an embodiment of the invention, more than two marker structures can be used.

When focus is one of the process parameters that is measured using one of the embodiments disclosed herein, further optimization may be possible by employing one of the following techniques. In an embodiment of the invention, in order to create a larger change in spectral shape per nanometer of defocus, smaller marker structures can be used, since these structures have a smaller depth of focus. In another embodiment of the invention, in order to increase the sensitivity to focus changes, structures with more side wall, e.g. the use of semi isolated contact holes or semi isolated dots instead of lines may be used. In another embodiment of the invention, it may also be possible to use a resist that shows a larger spectral change with defocus. In a production situation, however, this option may not be applicable.

It should be understood that any type of substrate, e.g. product wafers or test wafers, may be used in applications of embodiments of the present invention. It should also be understood that the actual, physical structure to be measured may be located anywhere on the substrate, e.g. within a chip area or a in a scribe-lane, as may be desirable in such application. Furthermore, the light spot of the scatterometer, may be as large as the chip area or an exposure field, in embodiments of the invention. A spot of this size may allow a fast determination of the offset per chip and field respectively.

It may be desirable to arrange the lithographic process parameters, like focus and dose values across a FEM, in a shuffled way. Otherwise, a process parameter may increase from one side of the substrate to the other. As a result, process variations originating from sources outside the lithographic apparatus, which generally are linear across and/or rotationally symmetric with respect to the center of the substrate, could have a significant influence on the calibration results. By shuffling the values across a FEM, for example, the externally induced process parameters can significantly be eliminated.

In an embodiment of the invention, for qualification purposes, mini-FEM may be used to eliminate the externally induced process variation. This FEM only covers a small part of the substrate. Therefore, externally induced process variations are assumed to be negligible.

In a production process many identical wafers are generally processed one after the other. Once the optimal settings of a lithographic apparatus for a particular lithographic production process have been determined, these settings have to be kept within tight control limits. These settings may be maintained in an embodiment of the invention by automated process control (APC). In such a case, regular measurements on production wafers will be performed, thereby allowing feed back control.

The invention may be employed separately for a track and a lithographic apparatus. The invention can be used to twist knobs on a track or lithographic apparatus, not directly related to the process parameters to control. By measuring the relevant process parameters afterwards and employing the present invention, the effects of this knob twisting can be deduced, and an optimal setting of the knobs can be chosen. In contrast to the past, the use of offline measurements to obtain desired information employing techniques like scanning electron microscopy (SEM) and electrical line width measurements (ELM) can be avoided.

Figure 9:
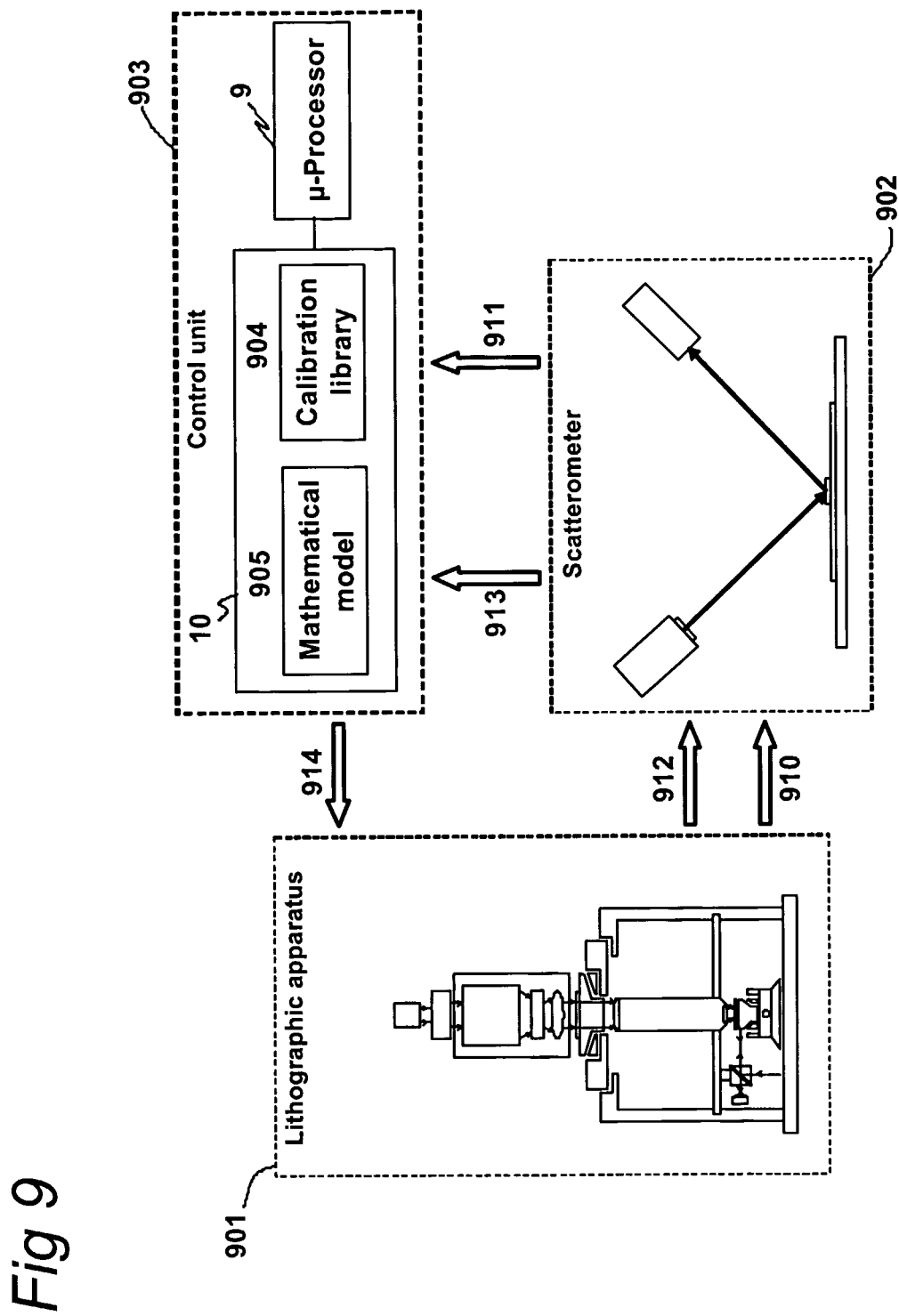
FIG. 9 depicts a lithography system according to an embodiment of the present invention.

FIG. 9 depicts a lithography system according to an embodiment of the present invention. In this embodiment, the substrate, which is exposed with the lithographic apparatus 901, is transferred (after development by the track) to the scatterometer 902. The scatterometer 902 is connected to a control unit 903 that includes a processor 9 and a memory 10. The lithographic apparatus 901 first creates a FEM, by printing a marker structure, suitable for scatterometric measurements, using predetermined settings for the process parameters focus and dose. Then, the substrate is transported 910 to the scatterometer 902. The scatterometer 902 measures calibration spectra and stores 911 the measured spectra in a calibration library 904 of memory 10.

Then the lithographic apparatus 901 patterns a production substrate with the same marker structure. Then, the substrate is transported 912 to scatterometer 902. The scatterometer 902 measures the spectrum of the light that is reflected from the marker structure generated by the lithographic apparatus 901. The spectrum is fed 913 into a mathematical model 905 that can be used by processor 9. The mathematical model 905 is used by processor 9 to compare the calibration spectra stored in calibration library 904, with the measured spectrum on the marker structure and the processor 9 derives the values of the parameters to be controlled, like dose and focus, by employing a regression technique.

Finally the processor 9 supplies 914 the derived values of these parameters to the lithographic apparatus 901. The lithographic apparatus 901 may use, for example, the derived values to monitor the drifts within the apparatus with respect to a reference state. The derived values are then used in feedback signals to correct for these drifts. In this case, the lithographic apparatus 901 is provided with a correction control unit, which uses the applied correction signals to compensate for drift. That correction control unit 903 may be configured to control, for example, the height of the substrate table WT to improve focus.

In an alternative embodiment of the invention, the derived values of these parameters are not supplied to the lithographic apparatus 901, but to a different entity, like a track, a computer terminal or a display. In the latter case, an operator, who is responsible for the operation of the lithographic apparatus 901, may then be able to check, for example, whether the derived values fall within the control limits or not. In another embodiment of the invention, the mathematical model 905 and/or the calibration library 904 may be located in a different entity than the control unit 903. In an embodiment of the invention, both the lithographic apparatus 901 and the scatterometer 902 may be connected to the same track in order to efficiently control the parameters of the lithographic apparatus 901. The derived values can also be used in a feed forward signal, which enables optimization of the settings of a next process task. The derived values can be sent, for example, to an etching apparatus, which can adapt its settings to the substrate that will arrive.

Examples of correctable effects for focus include the change of tilt within an exposure field, the change of offset across the wafer as well as offset from wafer to wafer. Examples of correctable effects for dose include the change of tilt and/or curvature within an exposure field, the change of offset across the wafer as well as offset from wafer to wafer.

According to an embodiment of this method, spectra are directly used to determine the values of the at least one process parameter without complicated calculations and required knowledge of the properties of the substrate. Moreover, the regression technique that is employed by the mathematical model reduces, in the process of extracting the relevant information from the spectra, the noise contribution to the acquired data. The optical detection apparatus may be a scatterometer. A scatterometer is configured to measure a spectrum in a fast and reliable fashion and can be used at many location on all kinds of substrates to be exposed.

According to an embodiment of the invention, measurements can be done on specially designed targets or on a device pattern within a chip area. In a further embodiment of the present invention, the at least one process parameter is selected from a group consisting of focus, exposure dose and overlay errors. There are also dose related parameters like 1) track parameters related to dose (e.g. PEB time/temperature), i.e. processing tasks with an effect similar to scanner exposure dose, and 2) variation of line width over the reticle, or variation from reticle-to-reticle. These effects can be corrected by the exposure dose and will also be interpreted by the model as exposure dose. Other process parameters of the group may include projection lens aberrations, flare for the projection lens, and the angular distribution of the light illuminating the mask, e.g. ellipticity. In an embodiment of the invention, separate determination of the values for one or more of these parameters can be achieved, these parameters being important to control the critical dimension uniformity in a lithographic process.

In an embodiment of the invention, the regression technique used by the mathematical model is selected from a group consisting of principal component regression, non-linear principal component regression, partial least squares modeling and non-linear partial least squares modeling.

In an embodiment of the invention, substrates that can be used include test wafers or product wafers. Depending on the particular application, the marker structure can be located on any position on the substrate. The marker structure thus may be positioned within the chip area or in the scribe-lane. When the marker structure is located within the chip area, it may be a part of a device pattern within that chip area. The freedom of positioning of the diffraction structure or using part of a device structure increases the versatility of the method of the present invention.

In an embodiment of the invention, the marker structure includes a diffraction grating. A diffraction grating is a structure well-suited for scatterometric applications.

In another embodiment of the present invention the method further includes preprocessing the obtained calibration data and the obtained measurement data before using the mathematical model. The use of preprocessing often leads to an increased performance of a mathematical model. Mathematical operations for pre-processing may include subtraction of a mean, division by standard deviation, selection of optical parameters and weighing of optical parameters. Examples of optical parameters are wavelength, angle and polarization state of the light beam that is used by the optical detection apparatus.

In an embodiment of the invention, at least one of the substrate and the calibration substrate includes at least two different marker structures. In the case of a product substrate, the at least two marker structures may be product marker structures whereas, in the case of a calibration substrate the at least two marker structures may be calibration marker structures. To keep the wording as simple as possible, the term "marker structure" used herein refers to both situations. The use of more than one marker structure may be extremely beneficial when preprocessing is used. The at least two marker structures may be placed in close proximity to each other, such that a distance between the at least two marker structures is in the same order of magnitude as a size of the marker structures.

In an embodiment of the invention, the at least two marker structures include a first marker structure including a number of non-patterned layers; and a second marker structure including the same non-patterned layers on top of which a pattern is provided. In this embodiment, the first marker structure is only sensitive to variation of the non-patterned layers. Any spectral changes due to variations in the non-patterned layers can be detected and used in the analysis of the spectrum obtained on the second marker structure.

In another embodiment of the invention, the at least two marker structures include a first marker structure including a pattern with isolated lines; and a second marker structure including a pattern with dense lines or isolated spaces. These marker structures may have a different sensitivity to process parameters like focus and dose. As a result, additional information may be obtained, which can be useful in the determination of the values of the process parameters by the mathematical model.

In an embodiment the lithographic apparatus is connected to a track and the optical detection apparatus is a scatterometer, which is connected to the same track. This enables an efficient way to monitor and adapt the parameters for a uniform performance of the lithographic apparatus.

At least some embodiments of the invention combine the beneficial influence of preprocessing for the performance of the mathematical model and the advantages of the use of more than one marker structure to obtain the required information. Mathematical operations that are suitable include subtraction of a mean, division by standard deviation, selection of optical parameters and weighing of optical parameters. The optical parameters are parameters like wavelength, angle and polarization state of the light used by the optical detection apparatus.

In an embodiment of the invention, the at least two calibration marker structures include a first calibration marker structure including a number of non-patterned layers; and a second calibration marker structure including the same non-patterned layers on top of which a pattern is provided. In this embodiment, the first calibration marker structure is only sensitive to variation of the non-patterned layers. Any spectral changes due to variations in the non-patterned layers can be detected and used in the analysis of the spectrum obtained on the first calibration marker structure.

In an embodiment of the invention, the at least two calibration marker structures include a first calibration marker structure including a pattern with isolated lines; and a second calibration marker structure including a pattern with either dense lines or isolated spaces. These marker structures may have a different sensitivity to process parameters like focus and dose. As a result, additional information is obtained, which can be useful in the determination of the values of the process parameters by the mathematical model.

In applications of embodiments of the invention, the calibration may generally be performed off-line. In an embodiment of the invention, the measurements, after finishing the calibration, are performed on-line, since obstruction of a process line is not desired. In an embodiment of the invention, the scatterometer may be integrated in the track to enable the on-line operation. Alternatively, a few substrates that have finished their process run can be measured by a stand-alone scatterometer, while the processing continues. In the latter case, however, the feedback interval may increase considerably. When the natural variation, which is present on substrates (e.g. production wafers) for calibration, is known in advance, e.g. by measurement, both calibration and measurement can be done on-line.

Experimental results: In an experiment two types of wafers with a diameter of 300 mm were exposed.

The first type was a flat calibration wafer on which a FEM was exposed. The FEM consisted of 13 focus steps (step size 30 nm) and 9 dose steps (step size 0.5 mJ/cm$^2$, around a nominal dose of 29 mJ/cm$^2$). For each structure, printed with an unique focus and dose value, spectra were measured with a scatterometer. These spectra, combined with the used focus and dose offsets, were used to create a regression model.

The second type of wafer was a sampled wafer, i.e. a wafer to be measured. In the experiment, two sampled wafers have been measured. Both sampled wafers contained indentations, deliberately created in the wafer to obtain more pronounced focus effect. Fields covering the whole wafer were exposed with one setting of focus and dose. Due to natural variation in focus and dose, each exposed pattern will however correspond to a slightly different focus and dose value than the ones that are set as explained before. The printed structures were subsequently measured by scatterometry. Using the regression model obtained from the FEM, each of the spectra belonging to the printed structures of the sample wafers was translated into a focus and dose value.

Applying the above mentioned regression model to the spectra from the sampled wafers with indentations, resulted in a focus and a dose distribution. To verify the accuracy of the scatterometry results, the correlation to another well-established method was established. In this experiment, such a correlation is only established for focus by comparing the results with results from a so-called leveling verification test (LVT), a test for instance discussed in Valley et al., SPIE USE V.1 5375-132 (2004). This test uses a reticle-type substrate with wedged-thickness areas, for instance formed by providing a large number of small prisms, each prism being fixed above a marker structure suitable for measuring overlay. The reticle-type substrate furthermore comprises a number of "normal" marker structures that are available for reference. The lateral shift versus defocus for the marker structures "underneath" the prisms, results in a nearly linear relation between image displacement and defocus. Consequently, focus errors are translated into overlay errors. After measuring the wafer with the scatterometer, the wafer was stripped, recoated and re-exposed for the LVT-measurement.

The LVT-data have been interpolated to the scatterometry measurement grid. A very good correlation between both techniques is observed as can be seen in table 1. Table 1 gives the differences in focus measured by LVT and scatterometry for the two sampled wafers and two types of recorded scatterometry spectra, called $\alpha$ and $\beta^2$. The correlation is presented as the $3\sigma$-focus difference (dF) between both techniques, the regression slope (slope) and correlation coefficient $R^2$. The correlation results are very similar for both wafers and do not depend strongly on the type of spectrum used. The upper limit for the scatterometry accuracy is given by the focus difference between both techniques. The real accuracy will be better since LVT also has a certain inaccuracy and the wafer has been recoated and re-exposed in between the two measurements.

TABLE 1

Focus differences between scatterometry and LVT.

|  | dF [nm, 3σ] | slope | $R^2$ |
|---|---|---|---|
| Wafer 1, α | 36 | 0.88 | 0.85 |
| Wafer 1, β | 36 | 0.87 | 0.76 |
| Wafer 2, α | 37 | 0.81 | 0.81 |
| Wafer 2, β | 36 | 0.81 | 0.74 |
| Average | 36 | 0.85 | 0.79 |

In the description above, it is assumed that the marker structure is illuminated after development. It is, however, also possible to use latent marker structures, i.e. a marker structure that is exposed, but not yet developed. Latent markers can be imaged shortly after exposure, which is advantageous since the feedback-loop can be faster. Furthermore, since track processing has not finished yet, the measurement data can be used for a feed forward signal to the track.

While specific embodiments of the invention have been described above, it will be appreciated that the invention may be practiced otherwise than as described. Embodiments of the invention also include computer programs (e.g. one or more sets or sequences of instructions) to control a lithographic apparatus to perform a method as described herein, and storage media (e.g. disks, semiconductor memory) storing one or more such programs in machine-readable form. The description is not intended to limit the invention. E.g., the invention may be applied in different technical areas, including areas like lithography, MRI and radar applications, and others. However, use of the invention in the area of lithography is especially advantageous because of it's complex and high-technological nature which makes it very difficult if not impossible to control all parameters to the desired level. By using the invention, parameters that cannot be controlled directly are controlled indirectly.

What is claimed is:

1. A method for determining at least one process parameter in a device manufacturing process, the method comprising:
   obtaining calibration spectral measurement data from a plurality of calibration marker structure sets provided on a calibration object, each of said plurality of calibration marker structure sets comprising at least one calibration marker structure, calibration marker structures of different calibration marker structure sets being created using different known values of said at least one process parameter;
   determining a mathematical model by using said known values of said at least one process parameter and by employing a multi-variant regression technique on said calibration spectral measurement data, said mathematical model comprising a number of regression coefficients;
   obtaining spectral measurement data from at least one marker structure provided on an object, said at least one marker structure being made using an unknown value of said at least one process parameter;
   comparing the obtained spectral measurement data with the calibration spectral measurement data to determine the unknown value of said at least one process parameter for said object from said obtained spectral measurement data by employing said regression coefficients of said mathematical model; and
   adjusting a control parameter of a lithographic apparatus based on the unknown value of said at least one process parameter for said object in the device manufacturing process;
   wherein the multi-variant regression technique used by the mathematical model is selected from a group consisting of principal component regression, non-linear principal component regression, partial least squares modeling and non-linear partial least squares modeling.

2. The method according to claim 1, wherein said calibration measurement data and said measurement data are obtained with an optical detector.

3. The method according to claim 2, wherein said optical detector is a scatterometer.

4. The method according to claim 1, wherein said object is a substrate.

5. The method according to claim 4, wherein the substrate comprises one of a group consisting of a test wafer and a product wafer.

6. The method according to claim 4, wherein the at least one marker structure is positioned on said substrate within one of the group consisting of a chip area and a scribe-lane.

7. The method according to claim 6, wherein the at least one marker structure is a part of a device pattern within a chip area.

8. The method according to claim 1, wherein the at least one marker structure comprises a diffraction grating.

9. A method for determining at least one process parameter in a device manufacturing process, the method comprising:
   obtaining calibration spectral measurement data from a plurality of calibration marker structure sets provided on a calibration object, each of said plurality of calibration marker structure sets comprising at least one calibration marker structure, calibration marker structures of different calibration marker structure sets being created using different known values of said at least one process parameter;

determining a mathematical model by using said known values of said at least one process parameter and by employing a multi-variant regression technique on said calibration spectral measurement data, said mathematical model comprising a number of regression coefficients;

obtaining spectral measurement data from at least one marker structure provided on an object, said at least one marker structure being made using an unknown value of said at least one process parameter;

comparing the obtained spectral measurement data with the calibration spectral measurement data to determine the unknown value of said at least one process parameter for said object from said obtained spectral measurement data by employing said regression coefficients of said mathematical model; and adjusting a control parameter of a lithographic apparatus based on the unknown value of said at least one process parameter for said object in the device manufacturing process;

wherein the method further comprises preprocessing the obtained calibration spectral measurement data and the obtained spectral measurement data before said employing said regression coefficients.

10. The method according to claim 9, wherein said preprocessing comprises performing on said data at least one of the group of mathematical operations consisting of subtraction of a mean, division by standard deviation, selection of optical parameters and weighing of optical parameters, and wherein the optical parameters comprise at least one of the group of parameters consisting of wavelength, angle and polarization state.

11. The method according to claim 1, wherein each of said plurality of calibration marker structure sets comprises at least a first and a different second calibration marker structure.

12. The method according to claim 11, wherein said first calibration marker structure comprises a number of non-patterned layers and said second calibration marker structure comprises the same non-patterned layers on top of which a pattern is provided.

13. The method according to claim 11, wherein said first calibration marker structure comprises a pattern with isolated lines and said second calibration marker structure comprises a pattern with dense lines or isolated spaces.

14. The method according to claim 11, wherein the first and second calibration marker structures are in close proximity to each other, such that a distance between the first and second calibration marker structure is in the same order of magnitude as a size of the first and second calibration marker structure.

15. The method according to claim 1, wherein at least one calibration structure within a calibration marker structure set and said marker structure have substantially comparable shapes.

16. The method according to claim 1, wherein said method is related to at least one of a lithographic apparatus and a track.

17. The method according to claim 16, wherein said at least one process parameter is selected from a group consisting of focus, exposure dose, overlay error, track parameters related to dose, variation of line width over reticle, variations from reticle-to-reticle, projection lens aberrations, projection lens flare, and angular distribution of light illuminating the reticle.

18. The method according to claim 16, wherein the lithographic apparatus comprises:

an illumination system configured to provide a beam of radiation;

a support structure configured to support a patterning structure, the patterning structure serving to impart the beam of radiation with a pattern in its cross-section;

a substrate table configured to hold a substrate; and a projection system configured to project the patterned beam onto a target portion of the substrate.

19. A system for determining at least one process parameter, the system comprising:

a detector arranged to obtain calibration spectral measurement data from a plurality of calibration marker structure sets provided on a calibration object, each of said plurality of calibration marker structure sets comprising at least one calibration marker structure, calibration marker structures of different calibration marker structure sets being created using different known values of said at least one process parameter;

a processor unit storing a mathematical model determined by using said known values of said at least one process parameter and by employing a multi-variant regression technique on said calibration spectral measurement data, said mathematical model comprising a number of regression coefficients;

said processor unit being arranged to obtain spectral measurement data from at least one marker structure provided on an object, said at least one marker structure being made using an unknown value of said at least one process parameter; and to compare the obtained spectral measurement data with the calibration spectral measurement data to determine the unknown value of said at least one process parameter for said object from said obtained spectral measurement data by employing said regression coefficients of said mathematical model;

wherein the multi-variant regression technique used by the mathematical model is selected from a group consisting of principal component regression, non-linear principal component regression, partial least squares modeling and non-linear partial least squares modeling.

20. The system according to claim 19, wherein said detector is an optical detector.

21. The system according to claim 20, wherein said optical detector is a scatterometer.

22. The system according to claim 19, wherein said object is a substrate.

23. The system according to claim 22, wherein the substrate comprises one of a group consisting of a test wafer and a product wafer.

24. The system according to claim 22, wherein the at least one marker structure is positioned on said substrate within one of the group consisting of a chip area and a scribe-lane.

25. The system according to claim 24, wherein the at least one marker structure is a part of a device pattern within a chip area.

26. The system according to claim 19, wherein the at least one marker structure comprises a diffraction grating.

27. A system for determining at least one process parameter, the system comprising:

a detector arranged to obtain calibration spectral measurement data from a plurality of calibration marker structure sets provided on a calibration object, each of said plurality of calibration marker structure sets comprising at least one calibration marker structure, calibration marker structures of different calibration marker structure sets being created using different known values of said at least one process parameter;

a processor unit storing a mathematical model determined by using said known values of said at least one process parameter and by employing a multi-variant regression technique on said calibration spectral measurement data, said mathematical model comprising a number of regression coefficients;

said processor unit being arranged to obtain spectral measurement data from at least one marker structure provided on an object, said at least one marker structure being made using an unknown value of said at least one process parameter; and to compare the obtained spectral measurement data with the calibration spectral measurement data to determine the unknown value of said at least one process parameter for said object from said obtained spectral measurement data by employing said regression coefficients of said mathematical model;

wherein the processor unit is arranged to preprocess the obtained measurement data before said employing said regression coefficients.

28. The system according to claim 27, wherein said preprocessing comprises performing on said data at least one of the group of mathematical operations consisting of subtraction of a mean, division by standard deviation, selection of optical parameters and weighing of optical parameters, and wherein the optical parameters comprise at least one of the group of parameters consisting of wavelength, angle and polarization state.

29. The system according to claim 19 wherein each of said plurality of calibration marker structure sets comprises at least a first and a different second calibration marker structure.

30. The system according to claim 29, wherein said first calibration marker structure comprises a number of non-patterned layers and said second calibration marker structure comprises the same non-patterned layers on top of which a pattern is provided.

31. The system according to claim 29, wherein said first calibration marker structure comprises a pattern with isolated lines and said second calibration marker structure comprises a pattern with dense lines or isolated spaces.

32. The system according to claim 29, wherein the first and second calibration marker structures are in close proximity to each other, such that a distance between the first and second calibration marker structure is in the same order of magnitude as a size of the first and second calibration marker structure.

33. The system according to claim 19, wherein at least one calibration structure within a calibration marker structure set and said marker structure have substantially comparable shapes.

34. The system according to claim 19, wherein said system comprises at least one of a lithographic apparatus and a track.

35. The system according to claim 34, wherein said at least one process parameter is selected from a group consisting of focus, exposure dose, overlay error, track parameters related to dose, variation of line width over reticle, variations from reticle-to-reticle, projection lens aberrations, projection lens flare, and angular distribution of light illuminating the reticle.

36. The system according to claim 34, comprising:
an illumination system configured to provide a beam of radiation;
a support structure configured to support a patterning structure, the patterning structure serving to impart the beam of radiation with a pattern in its cross-section;
a substrate table configured to hold a substrate; and
a projection system configured to project the patterned beam onto a target portion of the substrate.

* * * * *

UNITED STATES PATENT AND TRADEMARK OFFICE
CERTIFICATE OF CORRECTION

| | | |
|---|---|---|
| PATENT NO. | : 8,773,657 B2 | Page 1 of 1 |
| APPLICATION NO. | : 10/590352 | |
| DATED | : July 8, 2014 | |
| INVENTOR(S) | : Van Der Laan et al. | |

It is certified that error appears in the above-identified patent and that said Letters Patent is hereby corrected as shown below:

On Title Page, insert
-- [63] Continuation-in-part of application No. 10/853,724, filed on May 26, 2004, now abandoned. --

Signed and Sealed this
Ninth Day of December, 2014

Michelle K. Lee
*Deputy Director of the United States Patent and Trademark Office*